(12) United States Patent
Numada et al.

(10) Patent No.: US 8,185,177 B2
(45) Date of Patent: May 22, 2012

(54) NONINVASIVE LIVING BODY MEASURING DEVICE AND NONINVASIVE LIVING BODY MEASURING METHOD

(75) Inventors: Shigehiro Numada, Kobe (JP);
Toshiyuki Ozawa, Miki (JP)

(73) Assignee: Sysmex Corporation, Kobe (JP)

( * ) Notice: Subject to any disclaimer, the term of this patent is extended or adjusted under 35 U.S.C. 154(b) by 1249 days.

(21) Appl. No.: 11/904,983

(22) Filed: Sep. 28, 2007

(65) Prior Publication Data

US 2008/0081968 A1 Apr. 3, 2008

(30) Foreign Application Priority Data

Sep. 29, 2006 (JP) ................................ 2006-268930
Sep. 29, 2006 (JP) ................................ 2006-268931

(51) Int. Cl.
*A61B 5/00* (2006.01)
(52) U.S. Cl. ........................ 600/322; 600/310
(58) Field of Classification Search ................. 600/310, 600/322, 324, 326, 476, 477, 473; 422/82.05
See application file for complete search history.

(56) References Cited

U.S. PATENT DOCUMENTS

| 5,722,398 | A | * | 3/1998 | Ishihara et al. | ............... | 600/322 |
| 5,974,338 | A | | 10/1999 | Asano et al. | | |
| 5,983,120 | A | * | 11/1999 | Groner et al. | ................. | 600/310 |
| 6,061,583 | A | * | 5/2000 | Ishihara et al. | ............... | 600/322 |
| 6,104,939 | A | * | 8/2000 | Groner et al. | ................. | 600/322 |
| 6,846,288 | B2 | * | 1/2005 | Nagar et al. | .................. | 600/316 |
| 2004/0162471 | A1 | | 8/2004 | Ikeda et al. | | |
| 2006/0129037 | A1 | | 6/2006 | Kaufman et al. | | |

FOREIGN PATENT DOCUMENTS

| EP | 1447044 A1 | 8/2004 |
| EP | 1743570 A1 | 1/2007 |
| JP | 2007-044491 | 4/2007 |

OTHER PUBLICATIONS

European Search Report for Application No. EP 07018917 dated Feb. 7, 2008.

\* cited by examiner

*Primary Examiner* — Eric Winakur
*Assistant Examiner* — Chu Chuan (J J) Liu
(74) *Attorney, Agent, or Firm* — Brinks Hofer Gilson & Lione

(57) ABSTRACT

The present invention is to present a noninvasive living body measuring device that is capable of simplifying the structure and performing the analysis with accuracy in a short time. The noninvasive living body measuring device comprises: a light source for illuminating a living body which includes a blood vessel; an imaging part for imaging the illuminated living body to obtain a living body image; and an analyzing part for obtaining a density of a component contained in blood of the living body based on an image of the blood vessel in the living body image, and correcting the density of the component based on an image of a peripheral tissue of the blood vessel in the living body image.

6 Claims, 18 Drawing Sheets

NONINVASIVE LIVING BODY MEASURING DEVICE AND NONINVASIVE LIVING BODY MEASURING METHOD

RELATED APPLICATIONS

This application claims priority under 35 U.S.C. §119 to Japanese Patent Application No. 2006-268930 filed Sep. 29, 2006 and Japanese Patent Application No. 2006-268931 filed Sep. 29, 2006, the entire content of which is hereby incorporated by reference.

FIELD OF THE INVENTION

The present invention relates to a noninvasive living body measuring device and noninvasive living body measuring method for measuring a component contained in blood by analyzing blood vessels in an image of a living body obtained by imaging the living body.

BACKGROUND

Conventionally, a noninvasive living body measuring device which measures components such as hemoglobin and the like in blood by imaging a living body using an imaging means and analyzing blood vessels in the image of the living body, is disclosed in U.S. Patent Application Publication No. 2004-162471. The device disclosed in U.S. Patent Application Publication No. 2004-162471 is provided with a first light source for irradiating blood vessels (veins) in the wrist of a user, a light-receiving unit for detecting optical information from the blood vessels irradiated by the first light source, and an analyzing unit for analyzing the blood components flowing through the blood vessels based on the optical information. Thus, the user is able to continuously measure the components contained in blood simply by mounting the device on the wrist.

When measuring the components in blood using the device disclosed in U.S. Patent Application Publication No. 2004-162471, a band is mounted on the arm of the user nearer the heart than the wrist and the arm is pressurized with a predetermined pressure in order to facilitate imaging of the blood vessels. Thus, the blood flow of the wrist region is blocked and the blood vessels (veins) of the wrist expand.

When pressure is applied to the living body by the band, not only the target blood vessel but also the capillaries of the peripheral tissue around the target blood vessel are congested with blood. In the measurement of the components in blood, the amount of components in blood are determined based on the difference between the degree of brightness of the blood vessel and the degree of brightness of the surrounding area of the blood vessel in a captured image of the living body that includes the blood vessel. However, there may be only a small difference in the degrees of brightness when the surrounding tissues are congested with blood by the application of the pressure. Therefore, there is a problem that the measured value is smaller than the actual value.

Accordingly, the device disclosed in U.S. Patent Application Publication No. 2004-162471 is provided with a second light source for illuminating the surrounding tissue of the blood vessel in addition to the first light source, and a second light-receiving unit for detecting an optical information from the living tissue irradiated by the second light source, and the amount of the components in blood is corrected based on the optical information from the living tissue.

However, in the device disclosed in U.S. Patent Application Publication No. 2004-162471, a special light source and light-receiving unit are required to obtain the optical information from the living tissue surrounding the blood vessel in addition to the mechanism for obtaining optical information from the blood vessel which is the primary measurement target. Thus, the structure of the device becomes more complex. Furthermore, analysis of the components in blood takes time since the living body is not able to be imaged during the acquisition and analysis of the optical information from the living tissue surrounding the blood vessel.

Besides, the device of U.S. Patent Application Publication No. 2004-162471 is further provided with a third light source for illuminating the blood vessel by irradiating light in the same direction as that of the first light source, and the above mentioned light-receiving unit detects the optical information from the blood vessel illuminated by the first and third light sources. That is, the device of U.S. Patent Application Publication No. 2004-162471 is a reflective type device in which the light sources and imaging means are situated on one side of the living body. Since the light source is not able be disposed within the visual field of the imaging means in such a reflective type device, a uniform brightness within the visual field of the imaging means is difficult to achieve. Therefore, the light intensity from the first and third light sources has a great effect on the measurement accuracy. For this reason, it is important to adjust the light intensity from the first and third light sources in this reflective type noninvasive living body measuring device.

SUMMARY

A first aspect of the present invention is a noninvasive living body measuring device comprising: a light source for illuminating a living body which includes a blood vessel; an imaging part for imaging the illuminated living body to obtain a living body image; and an analyzing part for obtaining a density of a component contained in blood of the living body based on an image of the blood vessel in the living body image, and correcting the density of the component based on an image of a peripheral tissue of the blood vessel in the living body image.

A second aspect of the present invention is a noninvasive living body measuring device comprising: a light source for illuminating a living body which includes a blood vessel; an imaging part for imaging the illuminated living body to obtain a living body image; and an analyzing part for obtaining a value reflecting an amount of blood in a peripheral tissue of the blood vessel based on the living body image, and obtaining a density of a component contained in the blood of the living body, based on an image of the blood vessel in the living body image and the obtained value.

A third aspect of the present invention is a noninvasive living body measuring device comprising: a first light source for illuminating a living body which includes a blood vessel; a second light source for illuminating the living body, and which is disposed at a predetermined distance from the first light source; an imaging part for imaging the living body to obtain a living body image; an analyzing part for obtaining a density of a component in blood of the living body by analyzing an image of the blood vessel in the living body image; and a controller for controlling the imaging part so as to obtain a first living body image by imaging the living body illuminated by the first light source and obtain a second living body image by imaging the living body illuminated by the second light source, and adjusting a light intensity of each of the first and the second light sources based on the first living body image and the second living body image.

A fourth aspect of the present invention is a noninvasive living body measuring method comprising: a step of illuminating a living body which includes a blood vessel; a step of obtaining a living body image by imaging the illuminated living body; a step of obtaining a density of a component contained in blood of the living body based on an image of the blood vessel in the living body image; and a step of correcting the density of the component based on an image of a peripheral tissue of the blood vessel in the living body image.

A fifth aspect of the present invention is a noninvasive living body measuring method comprising: a step of illuminating a living body which includes a blood vessel by a first light source; a step of obtaining a first living body image by imaging the living body illuminated by the first light source; a step of illuminating the living body by a second light source; a step of obtaining a second living body image by imaging the living body illuminated by the second light source; a step of adjusting a light intensity of each of the first light source and the second light source based on the first living body image and the second living body image; a step of illuminating the living body by the first and the second light sources whose light intensity is adjusted; a step of obtaining a third living body image by imaging the living body illuminated by the first and the second light sources; and a step of analyzing an image of the blood vessel in the third living body image.

DETAILED DESCRIPTION OF THE EMBODIMENT

An embodiment of the noninvasive living body measuring device of the present invention is described in detail hereinafter with reference to the drawings.

Figure 1:
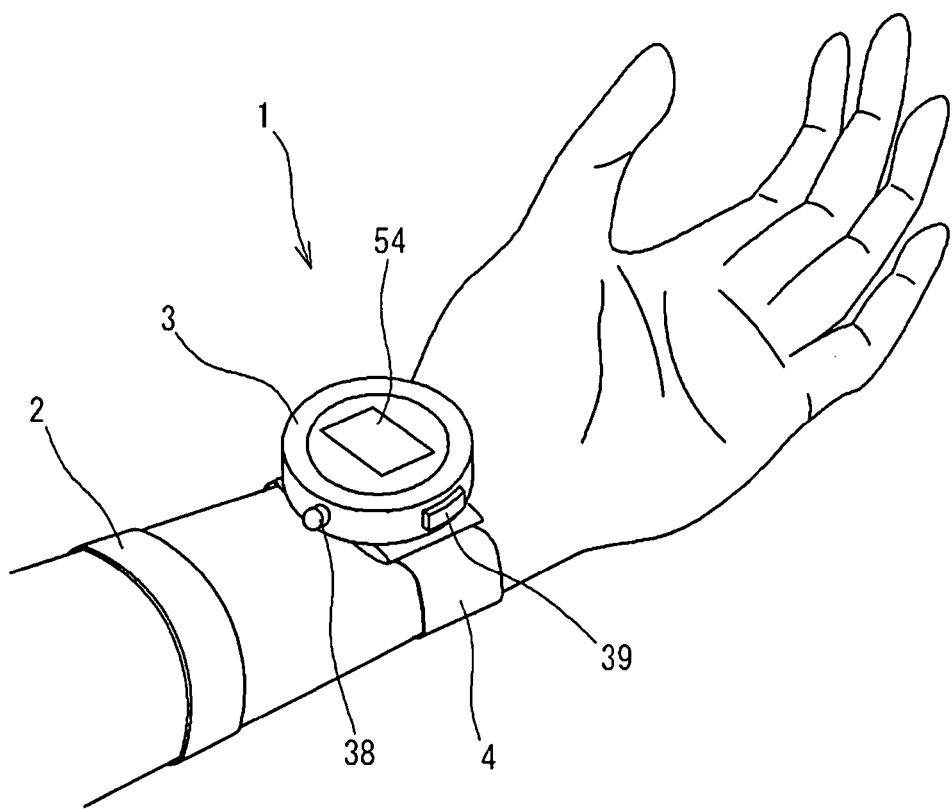
FIG. 1 shows the schematic structure of an embodiment of the noninvasive living body measuring device of the present invention.

FIG. 1 shows the schematic structure of a noninvasive living body measuring device 1 of an embodiment of the present invention. The noninvasive living body measuring device 1 is a wristwatch-type blood component analyzer provided with a device body 3 and a retainer part 4. The device body 3 is mounted on a human wrist by the retainer part 4. The device body 3 is mounted so as to be positionally adjustably in the circumference direction of the wrist via the retainer part 4. A power/execution key 38 and menu key 39 are provided on the side surface of the device body 3 to allow a user to operate the noninvasive living body measuring device 1. Furthermore, a band 2 is installed on the arm of the user at a position nearer to the heart than the wrist. The band 2 applies a predetermined pressure on the arm of the user to obstruct the blood flow in the vicinity of the wrist so as to expand the blood vessels (veins) in the wrist. Imaging of a blood vessel becomes easier when the measurement is carried out while the band 2 has increased the pressure on the wrist.

Figure 2:
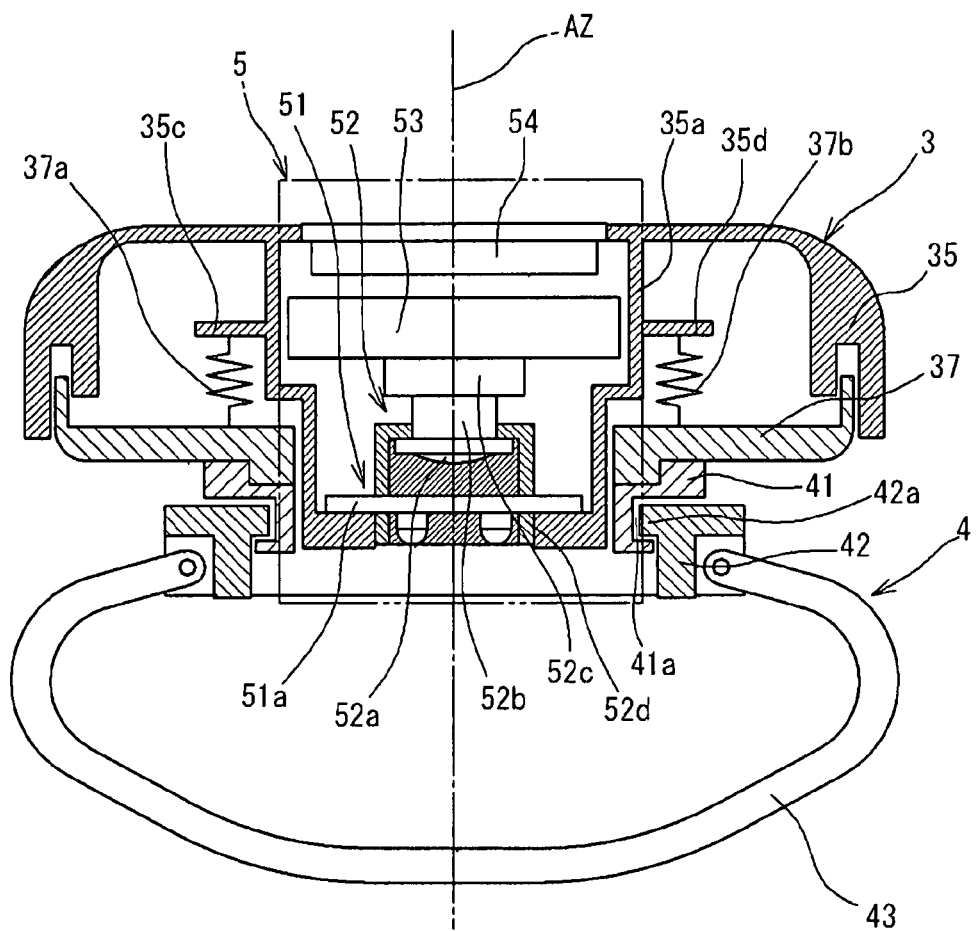
FIG. 2 is a cross section view of the noninvasive living body measuring device shown in FIG. 1.

FIG. 2 is a cross section view of the structure of the noninvasive living body measuring device 1. The device body 3 is provided with an exterior case 35, a rear cover 37 disposed on the rear side of the exterior case 35, and an engaging member 41. A cylindrically shaped unit retainer part 35a is formed in the center of the exterior case 35 to accommodate a measuring unit 5 which is described later. An empty space is formed in the center of the rear cover 37 and engaging member 41 to receive a unit retaining part 35a. A pair of projections 35c and 35d extends horizontally from the center part of the outer wall of the unit retainer part 35a. Compression springs 37a and 37b are respectively connected between the projection 35c and rear cover 37, and between the projection 35d and the rear cover 37. The exterior case 35 is forced toward the rear cover 37 by these compression springs 37a and 37b. Furthermore, a concave engaging part 41a is formed on the side surface of the engaging member 41, the engaging part 41a being capable of engaging an inward projection 42a of a support base 42 which is described later.

The retainer part 4 is configured by a support base 42 and a wrist band 43. The top surface of the support base 42 is rectangular in shape, and has a circular opening formed in the center part for the insertion of the engaging member 41 of the device body 3. The inward projection 42a is provided on the edge of the opening to engage the engaging member 41 so as to be pivotable on the axis AZ. The elastic rubber wrist band 43 is attached to the support base 42. The exterior case 35 and rear cover 37 are formed of a material that does not transmit light.

A measuring unit 5 is supported by the unit retainer part 35a. The measuring unit 5 is configured by a light source part 51, an imaging part 52, a control part 53, and a display part 54, and the light source part 51, imaging part 52, display part 54, and control part 53 are connected by wire cord, flat cable (not shown in the drawing) or the like so as to be capable of mutually exchanging electrical signals.

Figure 3:
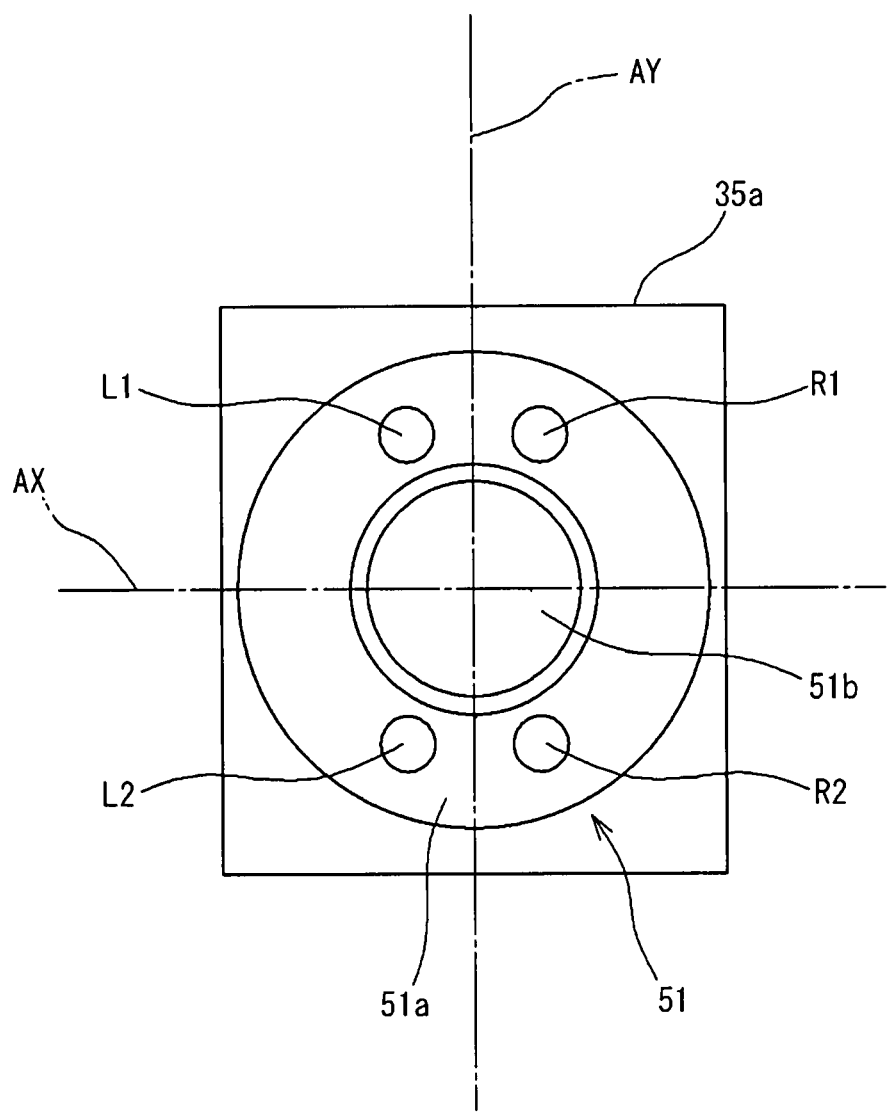
FIG. 3 is a top view showing the structure of the light source.

The light source part 51 is described below. FIG. 3 is a top view showing the structure of the light source. The light source part 51 is configured by a circular disk retaining plate 51a, and four light-emitting diodes R1, R2, L1, L2 held on the retaining plate 51a. A circular opening 51b is provided in the center of the retaining plate 51a to allow the transmission of light to the imaging part 52, and the light-emitting diodes mentioned above are arranged along the perimeter of the opening 51b.

Figure 4:
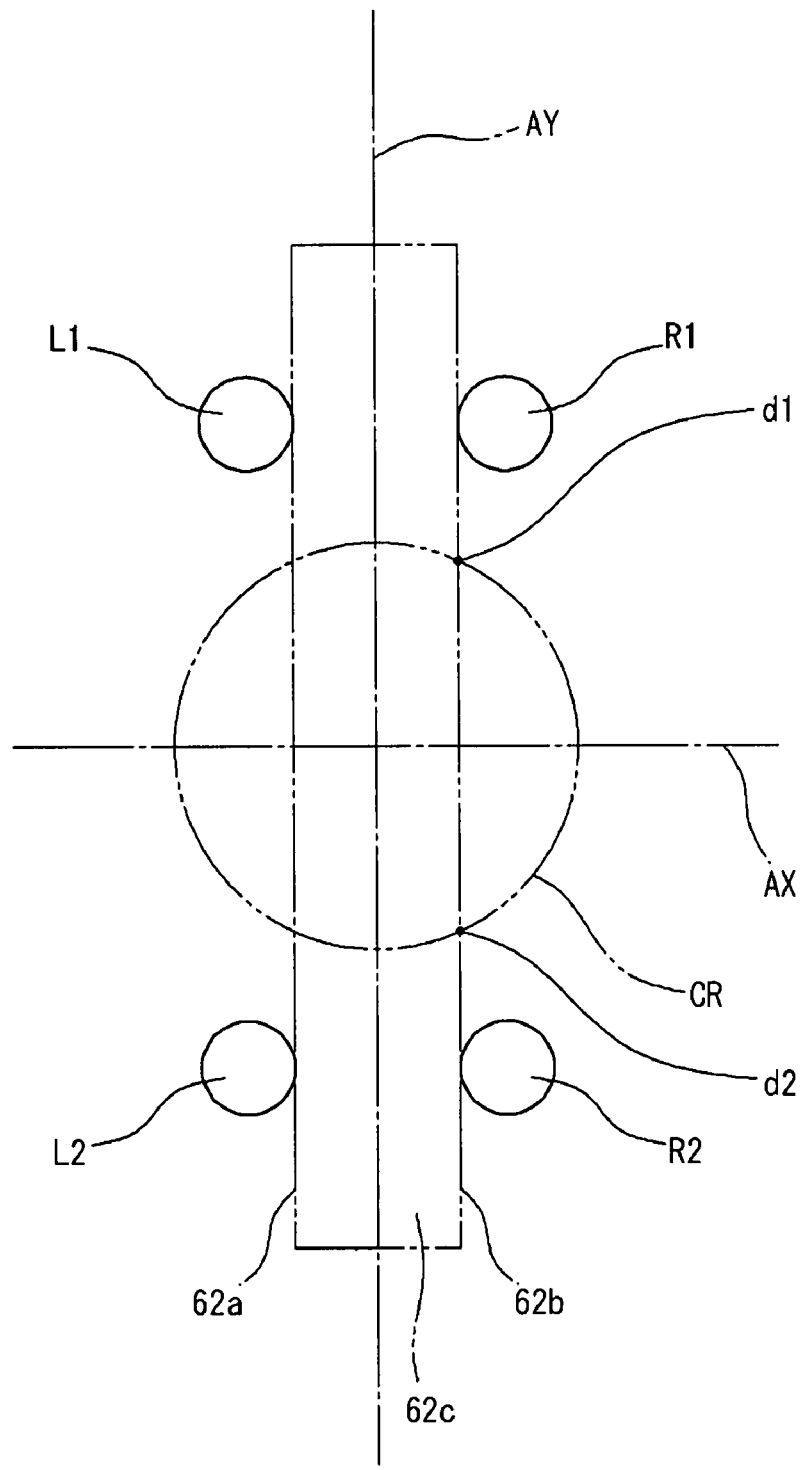
FIG. 4 shows the positional relationships of the light-emitting diodes provided on a retaining plate.

FIG. 4 shows the positional relationships of the four light-emitting diodes provided on the retaining plate 51a. The light-emitting diodes R1, R2, L1, and L2 are respectively disposed symmetrically with respect to a first axis AY and second axis AX which are mutually perpendicular and pass through the center of the opening 51b. When the noninvasive living body measuring device 1 is mounted on the wrist, the imaging region CR on the wrist surface is captured an image via the imaging part 52 and displayed on the display part 54.

A region 62c, which is disposed between an indicator line 62a at the side of the light-emitting diodes L1 and L2 (second light source) and an indicator line 62b at the side of the light-emitting diodes R1 and R2 (first light source), is a region suited for imaging by the imaging part 52, that is, a region positioned on a blood vessel when imaging. The indicator lines 62a and 62b are displayed on the display part 54 by the control part 53. When analysis of blood components is carried out, the mounting position of the device body 3 is adjusted so as to be positioned within the region 62c. The blood vessel is then bilaterally illuminated with near-infrared light (central wavelength of 805 nm) from the light-emitting diodes R1, R2, L1, and L2.

The structure of the imaging part 52 is described below. As shown in FIG. 2, the imaging part 52 is configured by a lens 52a for stopping down the focal point of the reflected light, a lens barrel 52b to which the lens 52a is fixedly attached, and a CCD camera 52c for imaging a living body; the imaging part 52 is capable of capturing an image of the imaging region CR. The lens 52a and lens barrel 52b are inserted in a cylindrical light-shielding barrel 52d which has a black colored interior. The CCD camera 52c sends the captured image to the control part 53 as image signals.

Figure 5:
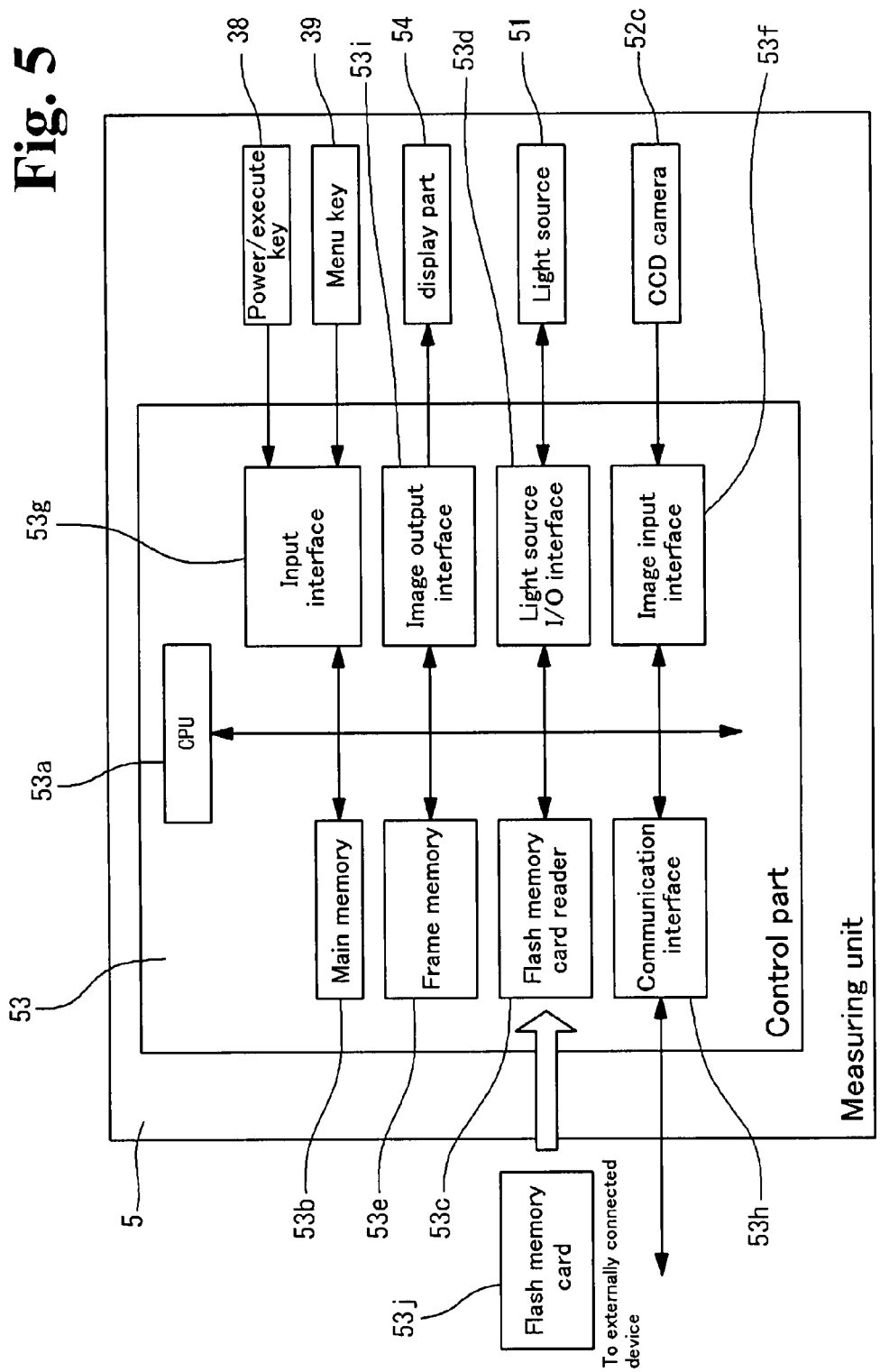
FIG. 5 is a block diagram showing the structure of the measuring unit.

The structure of the control part 53 is described below. The control part 53 is provided in the top part of the CCD camera 52c. FIG. 5 is a block diagram showing the structure of the measuring unit 5. The control part 53 is provided with a CPU 53a, a main memory 53b, a flash memory card reader 53c, a light source input/output interface 53d, a frame memory 53e, an image input interface 53f, an input interface 53f, a communication interface 53h, and an image output interface 53i. The CPU 53a, main memory 53b, flash memory card reader 53c, light source input/output interface 53d, frame memory 53e, image input interface 53f, input interface 53f, communication interface 53h, and image output interface 53i are connected by a data transmission line so as to be mutually transmit data. According to this configuration, the CPU 53a reads and writes data to and from the main memory 53b, flash memory card reader 53c, and frame memory 53e, and transmits data to the light source input/output interface 53d, image input interface 53f, input interface 53f, image output interface 53i, and communication interface 53h.

The CPU 53a, being an analyzing part, is capable of executing computer programs loaded in the main memory 53b and a ROM not shown in the drawing. The device functions as a noninvasive living body measuring device when the CPU 53a executes a computer program which is described later.

The main memory 53b is configured by an SRAM, DRAM or the like. The main memory 53b is used for reading the computer program stored on a flash memory card 53j and a ROM not shown in the drawing. The main memory 53b is further used as a work area for the CPU 53a when the computer program is executed.

The flash memory card reader 53c is used for reading data stored on the flash memory card 53j. The flash memory card 53j has a flash memory (not shown in the drawing), and can retain data even when external power is not supplied. The flash memory card 53j stores the computer program executed by the CPU 53a, and data used therewith.

An operating system, for example, can operating system conforming to TRON specifications, is also loaded on the flash memory card 53j. The operating system is not limited to the one example mentioned above inasmuch as the operating system may also provide a graphic user interface environment, such as, for example, Windows (registered trademark) of Microsoft Corporation, USA. In the following description, the computer program of the present embodiment operates on such an operating system.

The light source input/output interface 53d is configured by an analog interface such as a D/A converter, A/D converter or the like. The light source input/output interface 53d is electrically connected to the four light-emitting diodes R1, R2, L1, L2 provided in the light source 51 via an electrical signal line so as to control the operation of the light-emitting diodes. The light source input/output interface 53d controls the current flowing to the light-emitting diodes R1, R2, L1, L2 based on a computer program which is described later.

The frame memory 53e is configured by an SRAM, DRAM or the like. The frame memory 53e is used to store data when the image processing is executed by the light source input interface 53f which is described later.

The image input interface 53f is provided with a video digitizing circuit (not shown in the drawing) which includes an A/D converter. The image input interface 53f is electrically connected to the CCD camera 52c by an electrical signal line, and image signals from the CCD camera 52c are input to the image input interface 53f. The image signals received from the CCD camera 52c are subjected to A/D conversion by the image input interface 53f. The digitally converted image data are stored in the frame memory 53e.

The input interface 53g is configured by an analog interface such as an A/D converter. The power/execute key 38 and menu key 39 are electrically connected to the input interface 53g. According to this configuration, the operations of the device are selectable when the operator uses the menu key 39. The operator can also turn ON and OFF the power source of the device, and have selected operation executed by the device by using the power/execute key 38.

The communication interface 53h is configured by a serial interface such as, for example, a USB, IEEE1394, RS232C or the like, or a parallel interface such as SCSI or the like. The control part 53 can send and receive data to and from an externally connected device such as a portable computer or portable telephone using a predetermined communication protocol via the communication interface 53h. Thus, the control part 53 sends measurement result data to the externally connected device through the communication interface 53h.

The image output interface 53i is electrically connected to the display part 54, and outputs image signals to the display part 54 based on the image data received from the CPU 53a.

The display part 54 is described below. As shown in FIG. 2, the display part 54 is provided on the top part of the measuring unit 5, and is supported by the external case 35. The display part 54 is configured by a liquid crystal display, and displays screens in accordance with the image signals received from the image output interface 53i. The screen display is switchable in accordance with the condition of the noninvasive living body measuring device 1, for example, screens corresponding to a standby state, blood vessel position alignment state, and measurement completion state are displayed on the display part 54.

Figure 6:
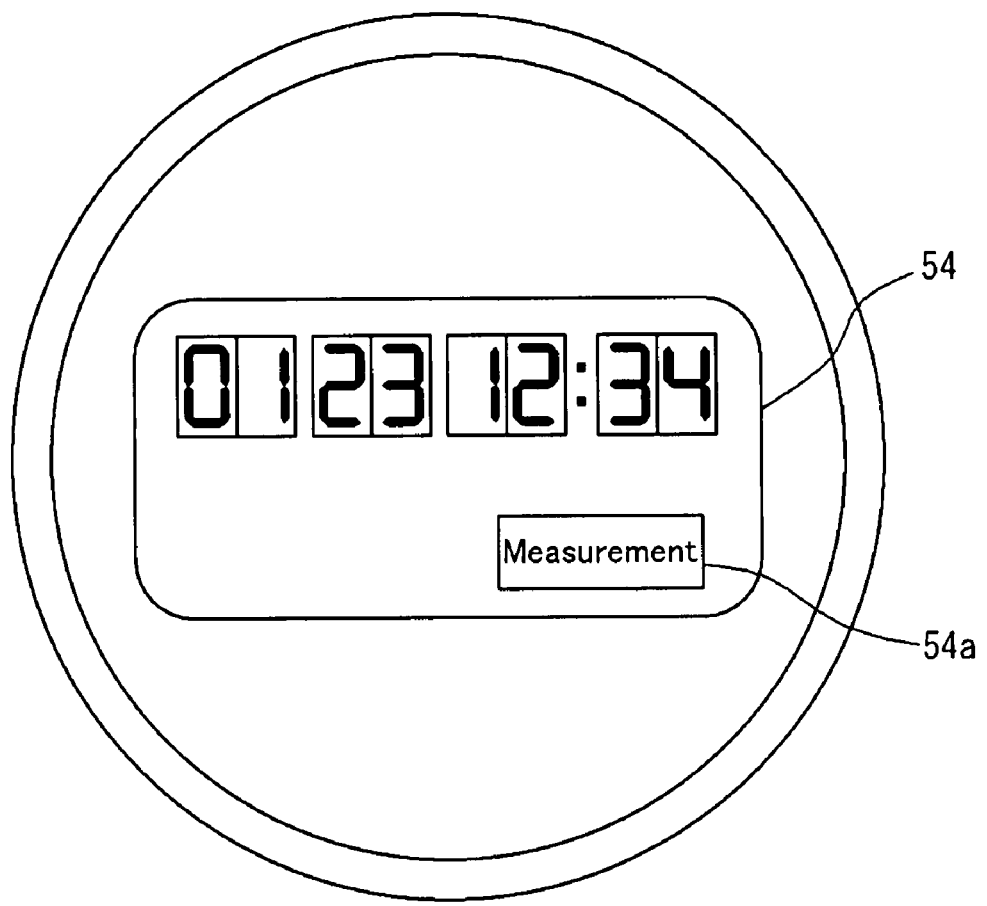
FIG. 6 shows an example of a screen displayed when the noninvasive living body measuring device is on standby condition.

FIG. 6 shows an example of a screen that is display when the noninvasive living body measuring device 1 is in a standby state. When the noninvasive living body measuring device 1 is in a standby state, the date and time are displayed in the center of the screen of the display part 54. A menu display area 54a is provided at the bottom right of the screen on the display part 54, and the operation of the noninvasive living body measuring device 1 is displayed when the power/execute key 38 is pressed, whereas "Measurement" is displayed in the standby state.

Figure 7:
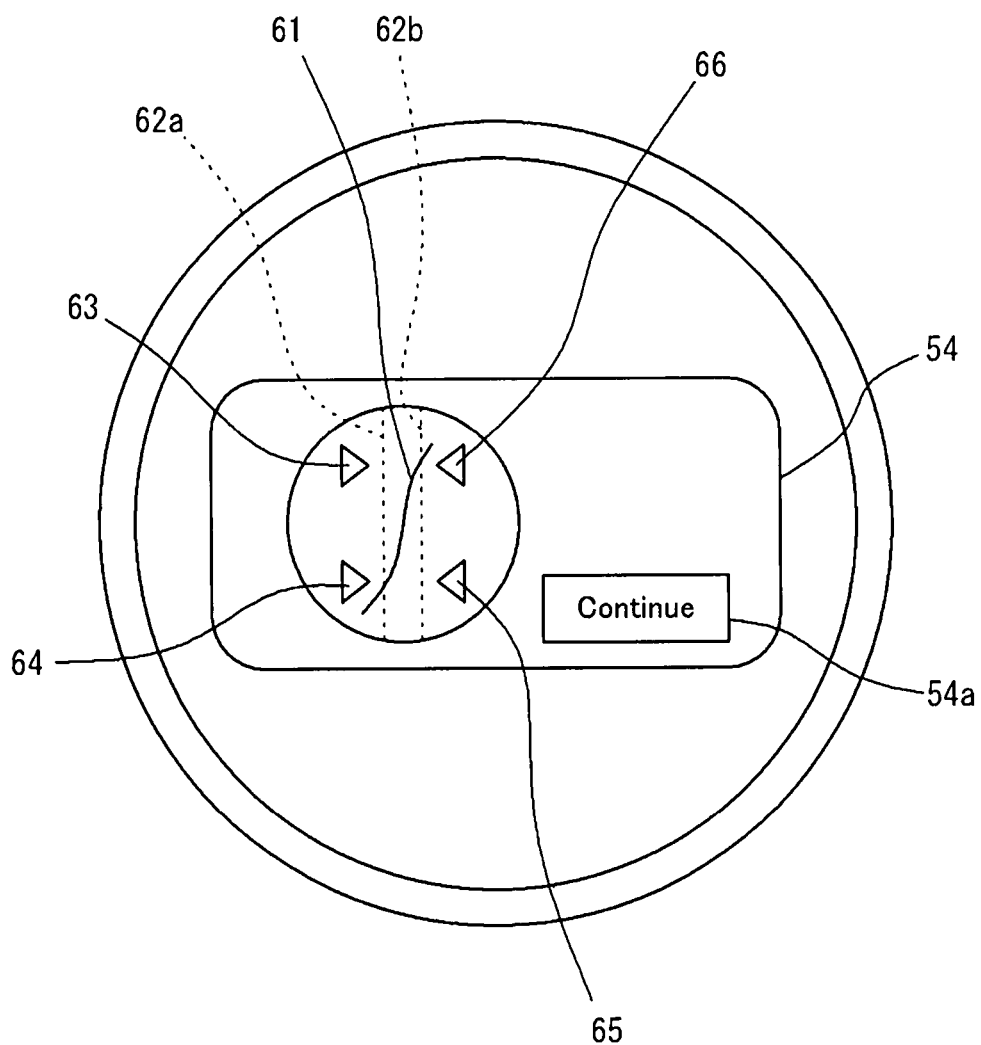
FIG. 7 shows an example of a screen displayed when the noninvasive living body measuring device is aligned with a blood vessel position.

FIG. 7 shows an example of a screen displayed when aligning a blood vessel position. In the noninvasive living body measuring device 1 of the present embodiment, the indicator lines 62a and 62b which represent a region suited for imaging by the imaging part 52 are displayed on the display part 54, so as to aid determination of whether or not the blood vessel image is positioned within a suitable region for imaging. When aligning the blood vessel position, the captured image and a blood vessel pattern 61 formed in a manner described later, as well as the indicator lines 62a and 62b represented in red are displayed. Markers 63, 64, 65, and 66 are displayed on the perimeter of the indicator lines 62a and 62b. Each marker may be lighted, such that when the blood vessel pattern 61 is not positioned so as to be accommodated within the region 62c between the indicator line 62a and the indicator line 62b, the control part 53 lights each of the markers to instruct the user in the direction in which to move the device body 3 so as to position the blood vessel pattern 61 within the region 62c.

Moving the device body 3 according to the lighted markers is described briefly below. In FIG. 7, when the markers 63 and 64 are lighted, the user must move the device body 3 to the right in FIG. 7, and when the markers 65 and 66 are lighted, the user must move the device body 3 to the left in FIG. 7. Furthermore, when the markers 63 and 65 are lighted, the user must rotate the device body 3 in a clockwise direction, and when the markers 64 and 66 are lighted, the user must rotate the device body 3 in a counterclockwise direction. For example, when the blood vessel pattern 61 is positioned as shown in FIG. 7, the control part 53 lights the markers 63 and 65 to prompt the user to rotate the device body 3 in a clockwise direction. According to this configuration, the position of the imaging part 52 is adjusted in a simple operation since the user can readily comprehend in which direction to move the device body 3 when adjusting the position of the imaging part 52 to a region suited for imaging a blood vessel.

The indicator line 62a and the indicator line 62b are displayed in red, when the blood vessel pattern 61 is not positioned within the region 62c (FIG. 4), and the indicator line 62a and the indicator line 62b are displayed in blue, when the blood vessel pattern 61 is positioned within the region 62c. Thus, the user can readily comprehend whether or not the blood vessel 61 is positioned within the region 62c.

When aligning the position of the blood vessel in this manner, "Continue" is displayed in the menu display region 54a; when the blood vessel pattern 61 is positioned within the region 62c, the indicator lines 62a and 62b are displayed in blue, the power/execute key 38 is enabled, and the user can continue measurement by pressing the power/execute key 38.

Figure 8:
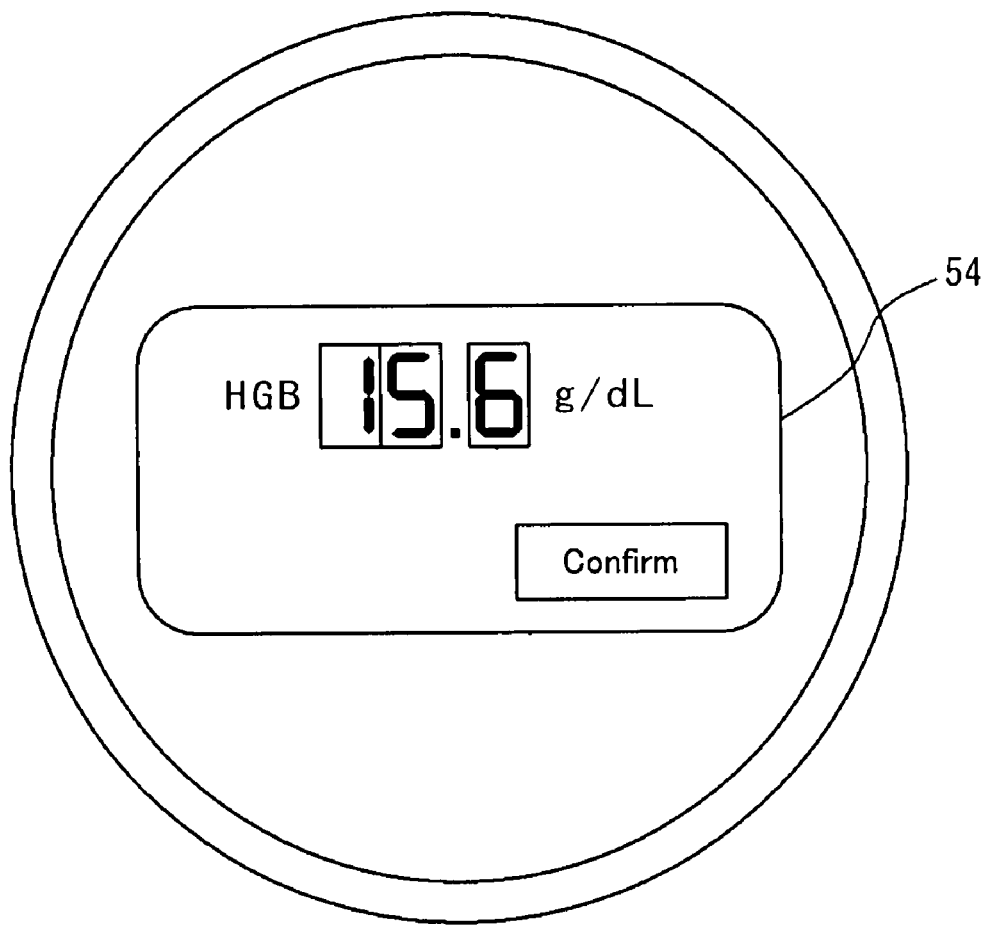
FIG. 8 shows an example of a screen displayed when the noninvasive living body measuring device completes a measurement.

FIG. 8 shows an example of a screen displayed when the noninvasive living body measuring device 1 completes a measurement. The result of the measurement of the blood component hemoglobin density is displayed on the display part 54 by digitally displaying "15.6 g/dl" to visually facilitate user comprehension. At this time, "Confirm" is displayed in the menu display region 54a.

Figure 9:
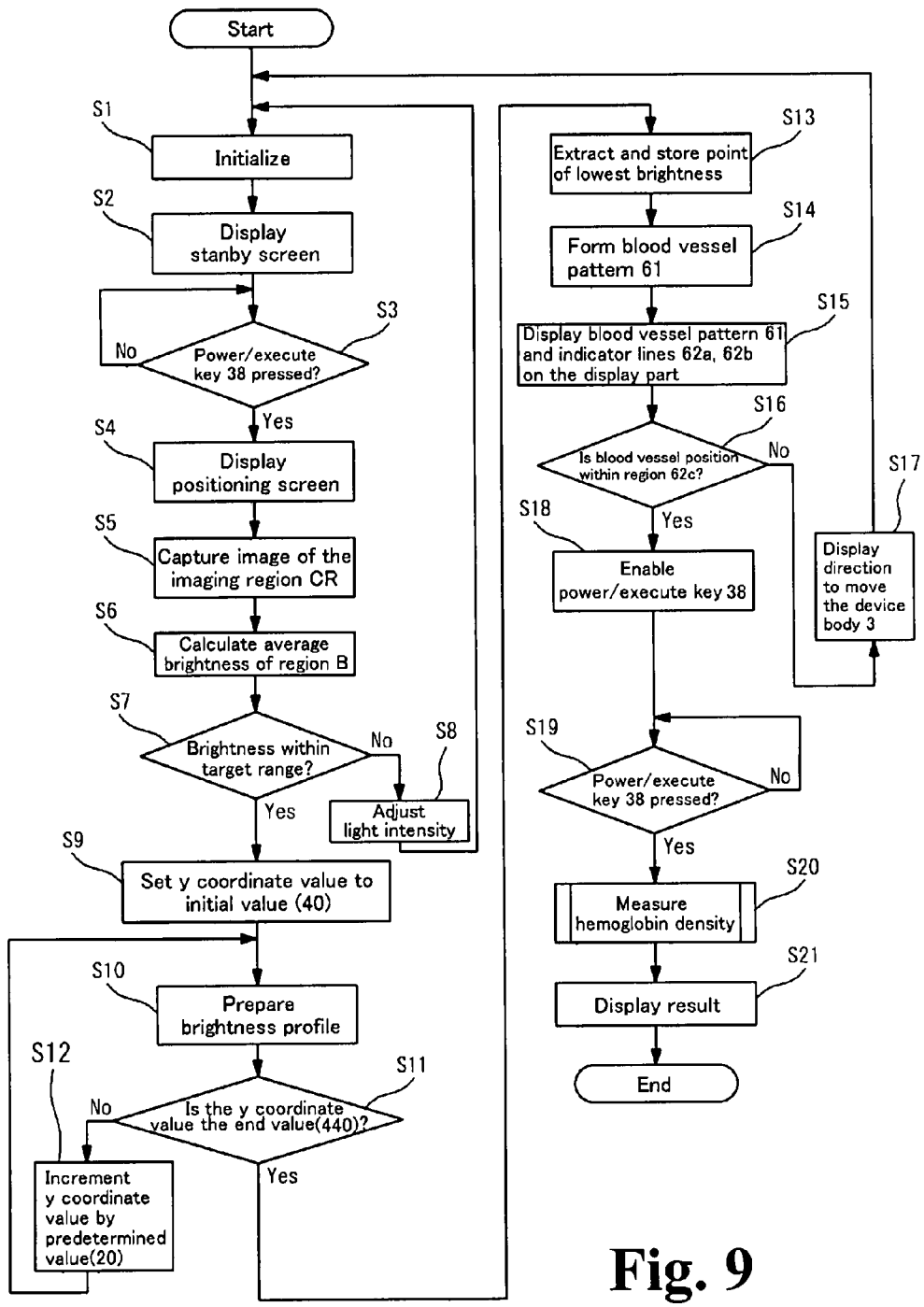
FIG. 9 is a flow chart of the measuring operation carried out by the noninvasive living body measuring device.

The measuring operation of the noninvasive living body measuring device 1 is described below. FIG. 9 is a flow chart of the measuring operation carried out by the noninvasive living body measuring device 1. First, the band 2 is installed on the user arm and the noninvasive living body measuring device 1 is mounted on the wrist, as shown in FIG. 1. At this time, a predetermined pressure is applied to the arm of the user by the band 2, blood flow is obstructed in the vicinity of the wrist, and the blood vessels of the wrist expand. Then, when the user turns on the power of the noninvasive living body measuring device 1 by pressing the power/execute key 38 provided on the noninvasive living body measuring device 1, the software is initialized and an operation check is performed on each part of the device (step S1). Thereafter, the device enters a standby state, and the standby screen of the standby state is displayed on the display part 54 as shown in FIG. 6 (step S2).

When the standby screen is displayed on the display part 54 and the user presses the power/execute key 38 (step S3: YES), the positioning screen show in FIG. 7 is displayed on the display part 54 (step S4). At this time, the CPU 53a lights the respective light-emitting diodes R1, R2, L1, L2 provided in the light source 51 by a predetermined intensity to illuminate the imaging region 62c (FIG. 4) and capture an image of the illuminated imaging region CR (step S5).

Figure 10:
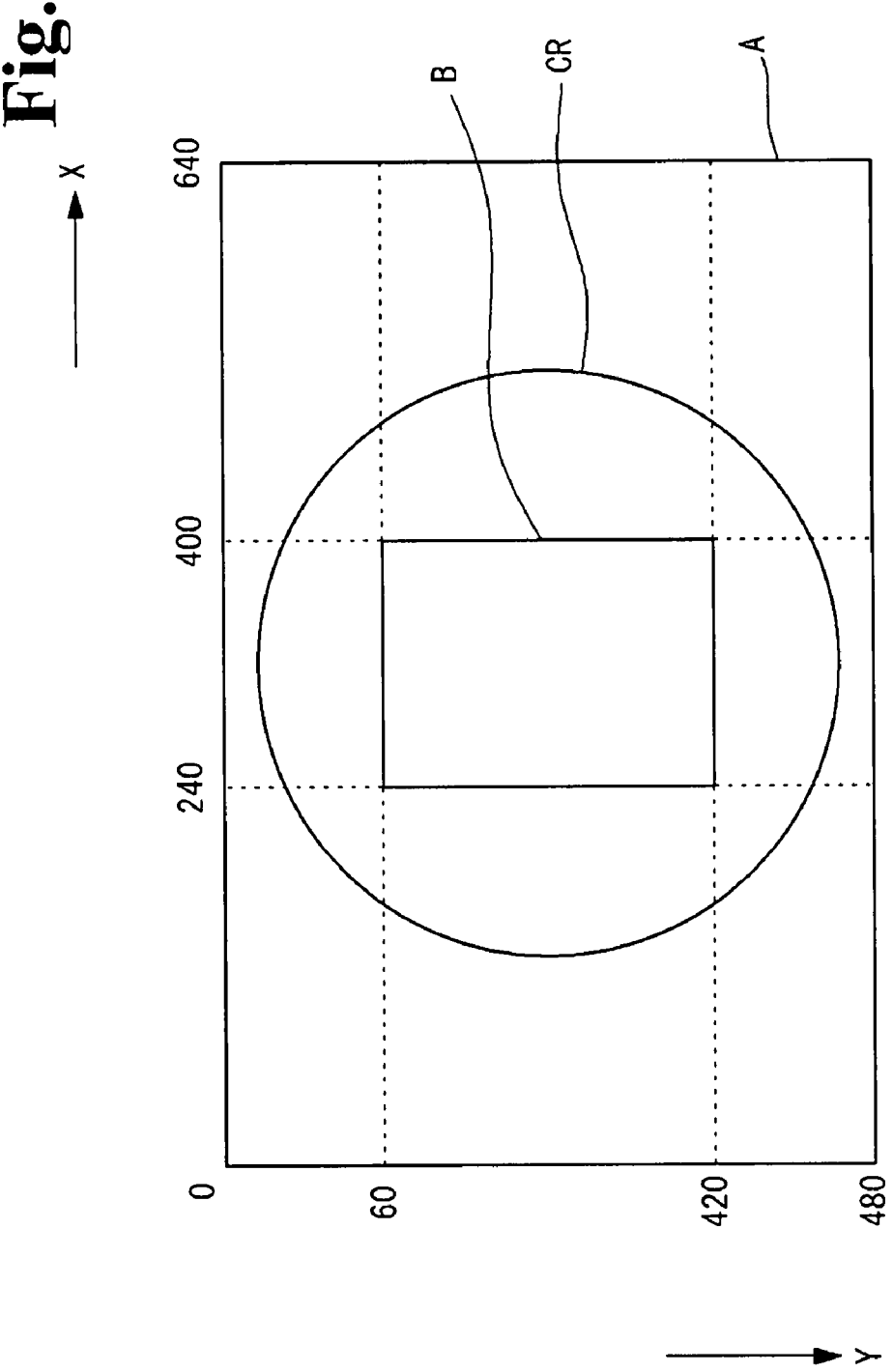
FIG. 10 is an illustration of coordinate divisions of a rectangular region which includes the imaging region CR on two-dimensional coordinates x and y in a range wherein 0x640 and 0y480.

FIG. 10 is an illustration of coordinate divisions of a rectangular region which includes the imaging region CR on two-dimensional coordinates x and y in a range wherein 0x640 and 0y480. As shown in FIG. 10, the CPU 53a divides the region A into two-dimensional coordinates x and y, designating a (0, 0) coordinate for the pixel at the topmost right of the rectangular region A that includes the image of the imaging region CR designated, and selecting four points (240, 0), (400, 60), 240, 420), and (400, 420) from among the points of the coordinate division. Then, the CPU 53a determines the average degree of brightness of the region B that circumscribes the four points (step S6). The coordinates which determine the region B are not limited to this example, and other coordinates may be used. The region B need not be a square shape, and may be a polygonal shape, or circle.

Then, the CPU 53a determines whether or not the brightness of the region B is within a target range (step S7). When the brightness of the region B is outside the target range, the amount of light is adjusted by adjusting the amount of current flowing to the light-emitting diodes R1, R2, L1, L2 using the light source input/output interface 53d, and the process returns to step S1. When the brightness of the region B is within the target range (step S7: YES), the CPU 53a sets the y coordinate value of the calculation object at an initial value (40) in a brightness profile which is described later. The brightness of the pixels is determined from end to end of the x coordinates at the set y coordinate value (40). Thus, a brightness profile (brightness profile PF) is determined for the pixels in the x direction at a predetermined y coordinate (step S1). Then, the CPU 53a determines whether the set y coordinate value is an end value (440). When the y coordinate value is not an end value (440) (step S11: NO), the CPU 53a increments the y coordinate value by a predetermined value (20) (step S12), and the process returns to step S10. When the y coordinate value is an end value (440) (step S11: YES), the CPU 53a extracts a point of lowest brightness (hereinafter referred to as lowest brightness point) in each extracted brightness profile, and stores the data in the frame memory 53e (step S13).

Figure 12:
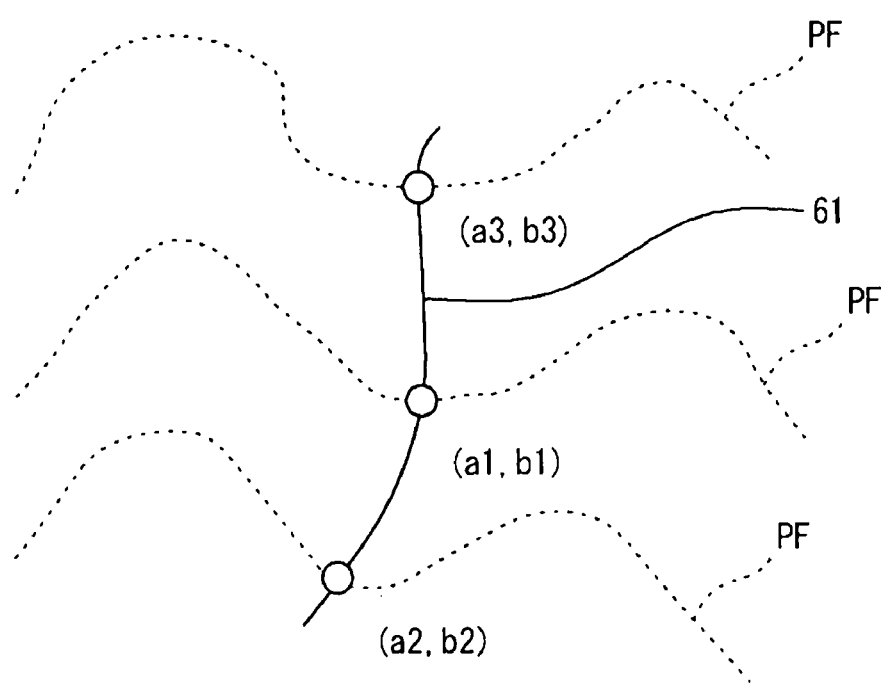
FIG. 12 illustrates a method for determining the position of a blood vessel.

FIG. 12 illustrates a method for determining the position of a blood vessel. As shown in FIG. 12, the CPU 53a connects the lowest brightness point (a1, b1) near the center of the image in the imaging region CR, and the adjacent lowest brightness points (a2, b2) and (a3, b3) in the vertical direction of the lowest brightness point (a1, b1). Then, the CPU 53a connects the lowest brightness point (a2, b2) and the adjacent points in the vertical direction, and connects the lowest brightness point (a3, b3) and the adjacent points in the vertical direction. The CPU 53a repeats this operation for the entire region of the image and extracts a blood vessel as a line sequence to form the blood vessel pattern 61 (step S14). As shown in FIG. 7, the CPU 53a displays an image of the captured imaging region CR on the display part 54, then the blood vessel pattern 61 formed in step S5, indicator lines 62a and 62b (FIG. 4) stored in the flash memory card 53j, and the markers 63, 64, 65, and 66 are displayed on the display part 54 (step S15). The CPU 53a then determines whether or not the blood vessel pattern 61 is positioned in the region 62c (FIG. 4) (step S16). When the blood vessel pattern 61 is not positioned in the region 62c (step S16: NO), the CPU 53a indicates the direction in which to move the device by 3 by lighting the markers 63, 64, 65, and 66 (step S17), then the process returns to step S1.

When the blood vessel pattern 61 is positioned within the region 62c (step S16: YES), the CPU 53a enables the power/execute key 38 so measurement can continue. At this time, the CPU 53a alerts the user via an audible alarm that the power/execute key 38 has been enabled (step S18). Then, the CPU 53a awaits input from the power/execute key 38 (step S19). When the user presses the power/execute key 38 to command that the measurement continue (step S19: YES), the CPU 53a carries out the hemoglobin density measurement (step S20), and displays the measurement result on the display part 54 as shown in FIG. 8 (step S21).

Figure 13:
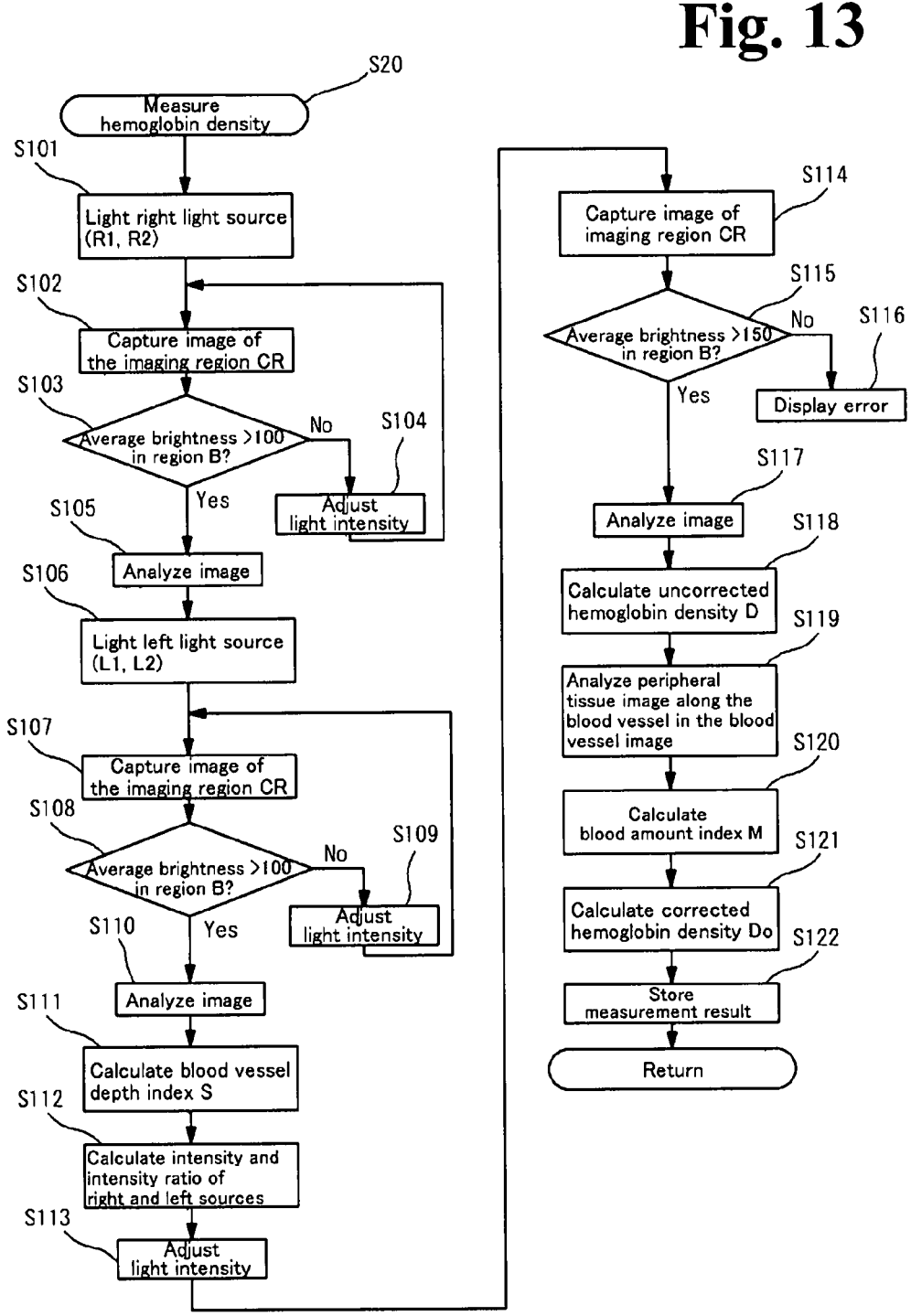
FIG. 13 is a flow chart showing details of the hemoglobin density measuring process executed in step S20 of the flow chart in FIG. 9.

FIG. 13 is a flow chart showing details of the hemoglobin density measuring process executed in step S20 of the flow chart in FIG. 9. The CPU 53a first controls the light source input/output interface 53d and illuminates the living body that includes the blood vessel with light of a suitable intensity by light-emitting diodes R1 and R2 of one of the light sources (first light source) among the light sources disposed on bilateral sides circumscribing the blood vessel (step S101), and captures an image using the imaging part 52 (step S102). Then, the CPU 53a determines whether or not the average brightness of the region B exceeds 100 (step S103). When the brightness does not exceed 100, the CPU 53a adjusts the intensity of the light of the light-emitting diodes R1 and R2 by adjusting the amount of current flowing to the light-emitting laser diodes R1 and R2 using the light source input-output interface 53d. Thereafter the process returns to step S102.

In the present embodiment, the brightness value is a digital conversion value (changeable 0 to 255) of an 8-bit A/D converter of the image input interface 53f. Since the brightness of the image and the size of the image signal received from the CCD camera 52c have a proportional relationship, the A/D conversion value (0 to 255) of the image signal used as the brightness value.

When the average brightness of the region B exceeds 100 (step S103: YES), the CPU 53a obtains a brightness profile PF1, and a density profile NP1 that is not dependent on the amount of incidence light of the image obtained in step S102 (step S105). The CPU 53a then controls the light source input/output interface 53d and illuminates the living body that includes the blood vessel with light of a suitable intensity by light-emitting diodes L1 and L2 of one of the light sources (second light source) among the light sources disposed on bilateral sides circumscribing the blood vessel (step S106), and captures an image using the imaging part 52 (step S107). Then, the CPU 53a determines whether or not the average brightness of the region B exceeds 100 (step S108). When the brightness does not exceed 100, the CPU 53a adjusts the intensity of the light of the light-emitting diodes L1 and L2 by increasing the amount of current flowing to the light-emitting laser diodes L1 and L2 using the light source input-output interface 53d. Thereafter the process returns to step S107.

When the average brightness of the region B exceeds 100 (step S108: YES), the CPU 53a carries out processing similar to that of step S105 for the image obtained in step S107, and obtains a brightness profile PF2, and a density profile NP2 that is not dependent on the amount of incidence light (step S110).

Figure 15:
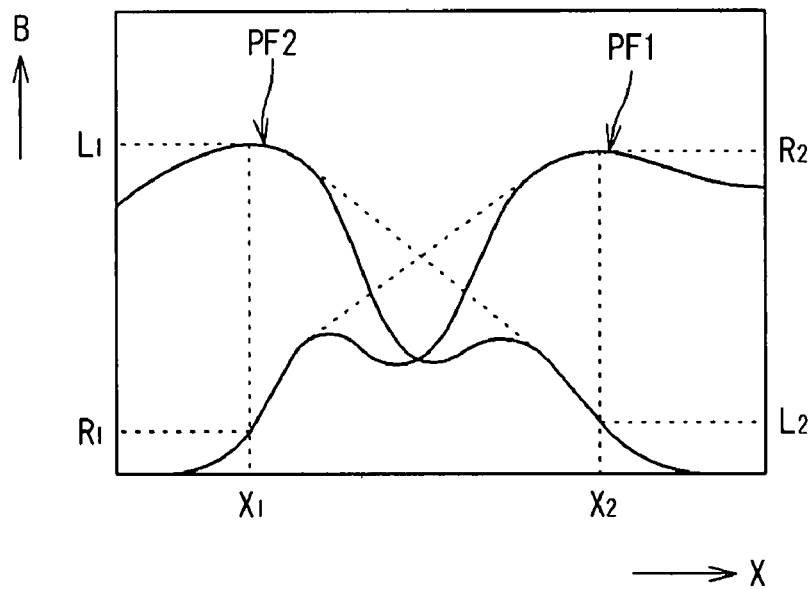
FIG. 15 shows the distribution of brightness B at position X.
Figure 16:
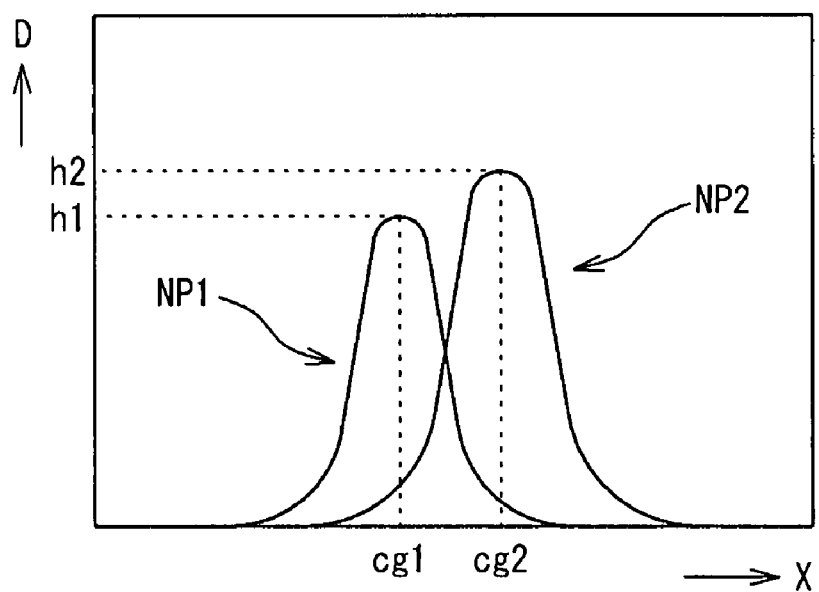
FIG. 16 shows the distribution of density D at position X.

FIG. 15 shows the distribution of the brightness B at position X using the brightness profiles PF1 is formed in step S105, and the brightness profiles PF2 is formed in step S110. FIG. 16 shows the distribution of the density D at position X using the density profile NP1 formed in step S105, and the density profile NP2 formed in step S110.

The CPU 53a acquires a peak height h1 and center of gravity coordinate cg1 from the density profile NP1 obtained in step S105, and acquires a peak height h2 and center of gravity cg2 from the density profile NP2 obtained in step S110. The CPU 53a then uses the acquired values to calculate a blood vessel index S by equation (1) below, and stores the calculation result in the frame memory 53e (step S111).

$$S=(cg2-cg1)/\{(h1+h2)/2\} \quad (1)$$

The CPU 53a also calculates the light intensity and intensity ratio of the light sources (light-emitting diodes R1 and R2 and light emitting diodes L1 and L2) on the right and left of the blood vessel based on the brightness profile PF1 obtained in step S105 and the brightness profile PF2 obtained in step S110 (step S112). Then the CPU 53a adjusts the light intensity of both light sources based on the obtained calculation result (step S113).

Specifically, a position of maximum brightness is designated x1 on the left half and a position of maximum brightness is designated x2 on the right half in a brightness profile (refer to FIG. 15) which is generated based on a right side lighted image obtained by lighting the right side (lighting the light-emitting diodes R1 and R2) (first light source), and a left side lighted image obtained by lighting the left side (lighting the light-emitting diodes L1 and L2) (second light source). Then, the brightness value at the position x1 is designated L1 and the brightness position x2 is designated L2 on the left side lighted brightness profile PF2, and the brightness value at the position x1 is designated R1, and the brightness value at position x2 is designated R2 on the right side lighted brightness profile PF1.

When the current values of the left and right light sources are represented as current value=(left, right), the current value when the left side is lighted is represented as current value=(CLeft, 0), and the current value when the right side is lighted is represented as (0, CRight), the allocation of the light source current to obtain a horizontal (uniform) brightness distribution when both sides are lighted may allocated in a ratio such that the current when one side is lighted is left:right=x:(1−x). That is, when both sides are lighted, the current value=(x (CLeft, (1−x)(Cright).

When x=(R1−R2)/{(L1−L2)−(R1−R2)}, x can be determined using the standardized values of L1, L2, R1, R2 as described above. For example, when x=0.4375 with the current value=(18, 0) when the left side is lighted and the current value=(0, 16) when the right side is lighted, the current value= (18×0.4375, 16×0.4375)≈(8, 9) when both sides are lighted. Thus, the light intensity of both light sources is adjustable for imaging the imaging region CR used in the hemoglobin density calculation (step S114), and the imaging region CR can be uniformly illuminated by light.

Then the CPU 53a controls the light source input/output interface 53d to illuminate the imaging region CR via the intensity adjusted light-emitting diodes R1, R2, L1, L2 to capture and image using the imaging part 52 (step S114). The CPU 53a then determines the average brightness of the region B as shown in FIG. 10, and determines whether or not the average brightness of the region B exceeds 150 in a process similar to step S106 (step S115). When the average brightness does not exceed 150, an error message is displayed (step S116).

Figure 11:
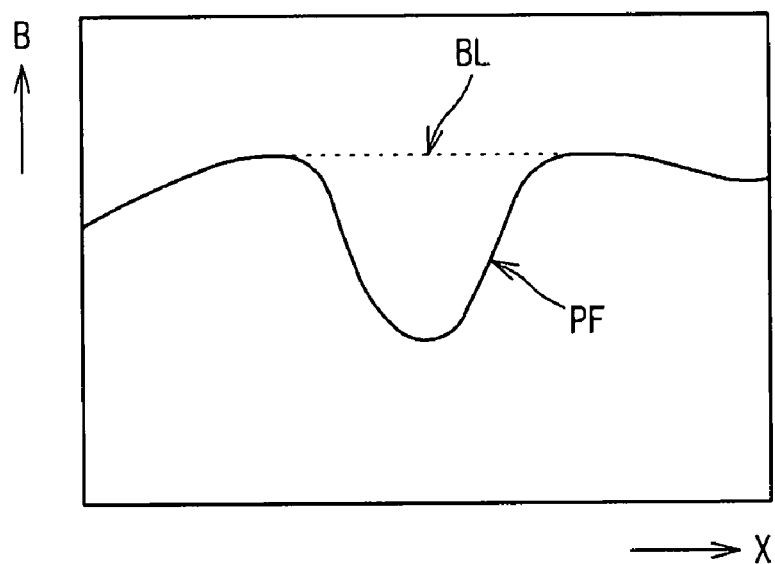
FIG. 11 shows an example of a brightness profile (brightness profile PF) of pixels in the x direction at a predetermined y coordinate.

When the average brightness of the region B does exceeds 150 (step S115: YES), the CPU 53a creates a brightness profile (distribution of the brightness B at position X) PF showing a first brightness distribution (FIG. 11) on the axis AX in the imaging region CR (FIG. 4), and the noise component is reduced using a method such as high speed Fourier transform or the like. The CPU 53a then standardizes the brightness profile PF by a baseline BL. The baseline BL is determined based on the shape of the brightness profile of the component absorbed by the blood vessel. Thus, a density profile (distribution of the density D at position X) NP that is not dependent on the amount of incidence light can be obtained (step S117).

Figure 14:
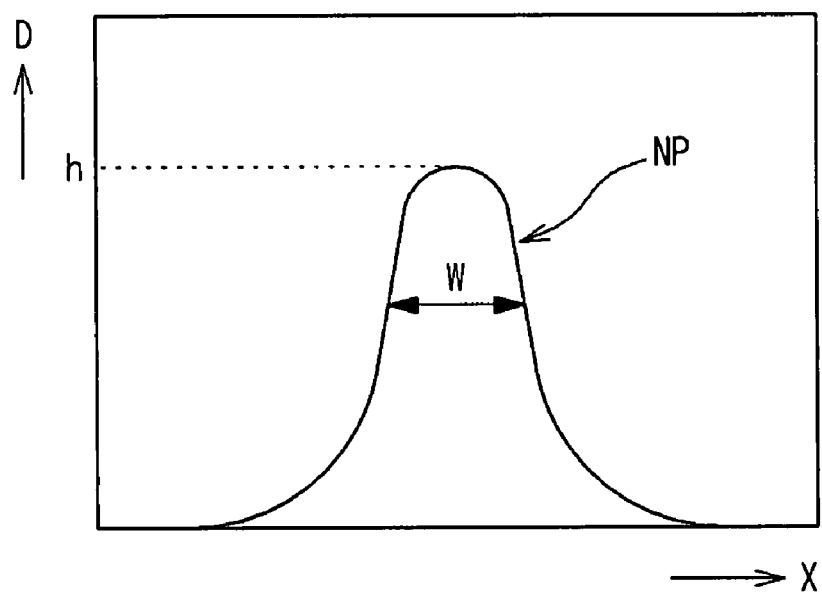
FIG. 14 shows the distribution of density D at position X.

FIG. 14 shows the distribution of the density D at position X, which forms the density profile NP as shown in the drawing. The CPU 53a then calculates the peak height h and peak half height w based on the formed density profile NP. The obtained h represents the light intensity ratio of the light that passes through the blood vessel (blood) and the light that passes through the tissue component of the measurement object, that is h represents the degree of the intensity of the light absorbed by the blood vessel, and w represents a length which is equivalent to the diameter of the blood vessel. The CPU 53a then calculates the uncorrected hemoglobin density D using equation (2) below, and stores the result in the frame memory 53e (step S118).

$$D = h/w^n \quad (2)$$

Where n is a constant that represents the nonlinear expanse of the peak half height caused by scattering. When there is no light scattering, n=1; and when there is light scattering, n>1.

The CPU 53a then analyzes the image of the tissue surrounding the blood vessel in the living body image obtained in step S114 (step S119), and calculates a blood amount index M that represents the amount of blood contained in the peripheral tissue (step S120). Specifically, a brightness distribution of the brightness distributed along the blood vessel image is calculated based on the blood vessel peripheral tissue image in the living body image at a predetermined distance (for example, 2.5 mm) from the blood vessel image in the living body image. Not only the target blood vessel but also the tissue surrounding the blood vessel is captured in the living body image. The brightness in the image attenuates in accordance with the exponential function of the distance from the light source to the irradiation position, and the percentage of attenuation of the brightness changes in proportion to the amount of blood in the tissue. Therefore, the amount of blood in the peripheral tissue can be estimated by calculating the attenuation rate of the brightness in the image of the peripheral tissue of the blood vessel.

The blood vessel is positioned so that the approximate center of the captured image is in a vertical cross section (vertical in FIGS. 3 and 4). Therefore, the calculation of this attenuation rate uses the brightness distribution on a line parallel to the blood vessel that extends from the blood vessel for a predetermined distance (for example, indicator line 62a or 62b in FIG. 4), or along a straight line (hereinafter referred to as the second brightness distribution relative to the brightness distribution of a horizontal cross section of the blood vessel (first brightness distribution).

Figure 17:
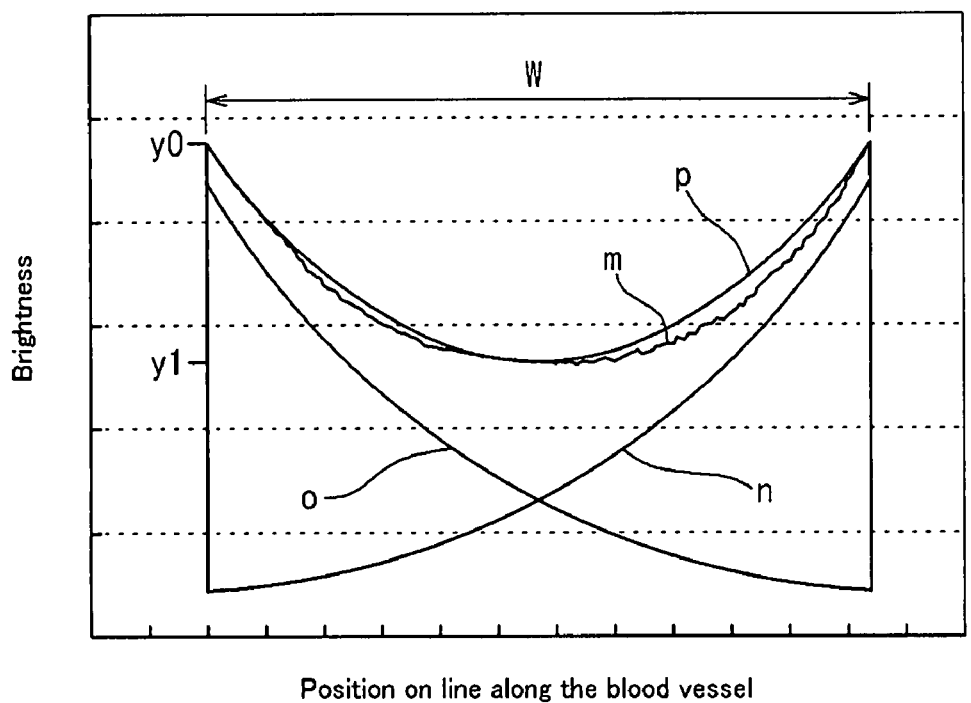
FIG. 17 shows an example of a second brightness distribution distributed along the blood vessel image.

Although the light from the light source attenuates according to the exponential function of the distance from the light source when the blood vessel peripheral tissue is approximately homogeneous, the second brightness distribution has a parabolic shape that superposes the exponential function so as to be mutually reverse since the light-emitting diode of the light source is disposed vertically in the imaging region CR (vertical in FIGS. 3 and 4). FIG. 17 shows an example of a second brightness distribution distributed along the blood vessel image. In FIG. 17, the vertical axis represents brightness, and the horizontal axis represents the position along the blood vessel image of the peripheral tissue in the captured image. For example, when the second brightness distribution is measured on the indicator line 62b (refer to FIG. 4), d1 and d2 on the horizontal axis approximately corresponds to points d1 and d2 at which the indicator line 62b intersects the circular imaging region CR, as shown in FIG. 4.

In FIG. 17, the parabolic curve m represents the actual measured brightness, and the exponential function n and exponential function o represent two exponential functions that separate the curve m into two parts by a method discussed below. The parabolic curve p is the theoretical superposition of the exponential function n and exponential function o, and matches the actual measured values.

To separate the parabolic curve m into the two parts of the exponential functions n and exponential function o, first the saturation-tinged parts at the bilateral ends are eliminated from the parabolic curve m, so that only the part actually forming the parabola remains. The brightness on the left end of this remaining part is designated y0, and the lowest brightness of the center is designated y1. The brightness of adjacent pixels are set at (r(100)% for each pixel, where r is defined as the attenuation rate.

The initial value U0 of the top light-emitting diode R1 and the initial value D0 of the bottom light-emitting diode R2 can be represented by equations (3) and (4) below, respectively, since the light from the top light-emitting diode R1 is 100% at the left end of the remaining part and the light from the bottom light-emitting diode R2 attenuates by the attenuation rate r to the power of w.

$$U0 = y0/(1+rw) \quad (3)$$

$$D0 = y0/(1+rw) \quad (4)$$

In the center, the light from the top light-emitting diode invariably attenuates by the attenuation rate r to the power of w/2, and can be represented by equation (5) below.

$$y1 = 2 \times U0 \times r^{w/2} = 2 \times y0/(1+rw) \times r^{w/2} \quad (5)$$

The attenuation rate r can be determined by solving for r in equation (5). When $r^{w/2} = X$, $y1 \times X^2 - 2y0 \times X + y1 = 0$, such that the attenuation rate r can be represented as shown below.

$$\left( \frac{y0 - \sqrt{y0 \cdot y0 - y1 \cdot y1}}{y1} \right)^{\frac{2}{w}}$$

In conventional methods such as that disclosed in United States Laid-Open Patent Publication No. 2004-162471, special light sources are used at two locations far and near, and the light from the light sources is detected by a photosensor. When the amount of light impinging the photosensor from the proximal side light source is designated v1, and the amount of light impinging the photosensor from the distal side light source is designated v2, the blood amount index M can be determined by M=log(v1/v2).

The definition of the attenuation rate r is that the brightness of adjacent pixels becomes (r(100)% for each pixel. In the conventional methods, therefore, when the distance (pixel position) from the proximal side light source to the photosensor is designated Ln and the distance (pixel position) from the distal side light source to the photosensor is designated Lf, the brightness for the distal side light source attenuates by a rate r to the power of Ln. Accordingly, it can be understood that M=log(C×rLn)/(C×rLf), and a value equal to the blood amount index M can be calculated using the attenuation rate r and substituting v1 and v2.

In the equation, C is the initial light intensity value of the light sources of the proximal side and distal side (light intensity not attenuated by the tissue).

The CPU 53a obtains a correction factor fs based on the blood vessel depth index S calculated in step S111, and obtains a correction factor fm based on the blood amount index M calculated in step S120. Then, a corrected hemoglobin density Do is calculated by the equation (6) below using the obtained values (step S121).

$$Do=D\times fs\times fm \qquad (6)$$

The CPU 53a stores the calculation result of step S121 in the frame memory 53e (step S122), and the process returns to the main routine.

Figure 18:
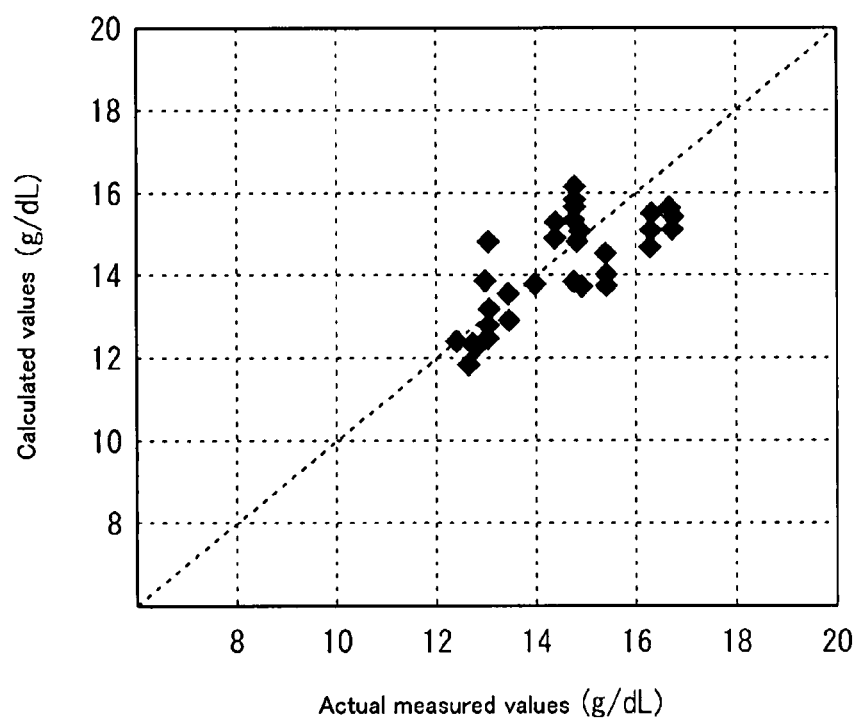
FIG. 18 is a graph plotting the calculation values of the noninvasive living body measuring device of an embodiment of the present invention and actual measurement values obtained from a hemocytometer or the like for the hemoglobin densities of a plurality of subjects.

FIG. 18 is a graph plotting the calculation values of the noninvasive living body measuring device of an embodiment of the present invention and actual measurement values obtained from a hemocytometer or the like for the hemoglobin densities of a plurality of subjects. As shown in FIG. 18, the actual measured values and the calculated values of the noninvasive living body measuring device 1 exists near a straight line which has a slope of 1, and it is understood that the noninvasive living body measuring device 1 measures hemoglobin density with a high precision because there is no disagreement between the actual measured values and the calculated values.

In the present embodiment described above, the light intensity of both light sources (first light source and second light source) is adjusted to obtain a captured image for use in calculating hemoglobin density based on a right side lighted image obtained by the right side lighting (light of the light-emitting diodes R1 and R2) and a left side lighted image obtained by left side lighting (light of light-emitting diodes L1 and L2). Thus, a right side lighted image (first living body image) which reflects the degree of brightness of the imaging region CR by right side lighting and a left side lighted image (second living body image) which reflects the degree of brightness of the imaging region CR by the left side lighting can be obtained by capturing images which are separately lighted by the right side light-emitting diodes R1 and R2 (first light source), and the left side light-emitting diodes L1 and L2 (second light source). From these living body images it is understood that the intensity of the light of each light source affects the brightness of the imaging region CR, and that the brightness of the imaging region CR can be rendered uniform by adjusting the degree of the intensity of the light of each light source. Accordingly, the light intensity of both light sources can be adjusted to obtain an intensity suited for imaging using the right side lighted image and the left side lighted image.

What is claimed is:

1. A noninvasive living body measuring device comprising:
   a light source for illuminating a region of a living body which includes a blood vessel;
   an imaging part for imaging the illuminated region of the living body to obtain a living body image; and
   an analyzing part for obtaining a density of a component contained in blood of the living body based on an image of the blood vessel in the living body image, and subsequently correcting the density of the component based on an image of a peripheral tissue of the blood vessel in the living body image.

2. The noninvasive living body measuring device of claim 1, wherein
   the analyzing part comprises a processor and a non-transitory computer readable storage medium having stored therein instructions executable by the processor for:
   generating a first brightness distribution information representing a first brightness distribution distributed across the blood vessel image in the living body image, based on the living body image;
   generating a second brightness distribution information representing a second brightness distribution distributed along the blood vessel image in the living body image, based on the living body image;
   obtaining the density of the component based on the first brightness distribution information; and
   correcting the density of the component based on the second brightness distribution information.

3. The noninvasive living body measuring device of claim 2, wherein
   the second brightness distribution information is generated based on the image of the peripheral tissue of the blood vessel at a predetermined distance from the blood vessel image in the living body image.

4. The noninvasive living body measuring device of claim 2, wherein
   correcting the density of the component based on the second brightness distribution information comprises determining a value reflecting an amount of the blood in the peripheral tissue of the blood vessel based on the second brightness distribution information, and correcting the density of the component based on the value reflecting an amount of the blood in the peripheral tissue of the blood vessel.

5. The noninvasive living body measuring device of claim 4, wherein
   determining the value reflecting an amount of the blood in the peripheral tissue of the blood vessel comprises determining an attenuation rate of a brightness in the second brightness distribution according to a distance from the light source as the value reflecting the amount of the blood in the peripheral tissue of the blood vessel.

6. A noninvasive living body measuring method comprising:
   a step of illuminating a region of a living body which includes a blood vessel;
   a step of obtaining a living body image by imaging the illuminated region of the living body;
   a step of obtaining a density of a component contained in blood of the living body based on an image of the blood vessel in the living body image; and
   a subsequent step of correcting the density of the component based on an image of a peripheral tissue of the blood vessel in the living body image.

* * * * *